United States Patent
Grate et al.

(10) Patent No.: US 10,500,228 B1
(45) Date of Patent: Dec. 10, 2019

(54) NANOPARTICLES, METHODS FOR PRODUCING NANOPARTICLES AND NANOPARTICLE GENERATORS

(71) Applicant: Battelle Memorial Institute, Richland, WA (US)

(72) Inventors: Jay W. Grate, West Richland, WA (US); Nigel D. Browning, Richland, WA (US); Patricia Abellan, Daresbury (GB)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 15/497,604

(22) Filed: Apr. 26, 2017

Related U.S. Application Data

(60) Provisional application No. 62/327,614, filed on Apr. 26, 2016.

(51) Int. Cl.
*B01J 19/06* (2006.01)
*A61K 33/24* (2019.01)
(Continued)

(52) U.S. Cl.
CPC ............ *A61K 33/24* (2013.01); *A61K 9/1611* (2013.01); *A61K 9/1682* (2013.01); *B01J 19/06* (2013.01);
(Continued)

(58) Field of Classification Search
CPC .... A61K 33/24; A61K 9/1682; A61K 9/1611; B01J 19/081; B01J 19/06;
(Continued)

(56) References Cited

FOREIGN PATENT DOCUMENTS

CN 101113010 A * 1/2008

OTHER PUBLICATIONS

Barta, Jan, Milan Pospisil, and Vaclav Cuba. "Indirect synthesis of Al2O3 via radiation-or photochemical formation of its hydrated precursors." Materials Research Bulletin 49 (2014): 633-639.*

(Continued)

*Primary Examiner* — Richard M Rump
(74) *Attorney, Agent, or Firm* — Wells St. Johns P.S.

(57) ABSTRACT

Compositions are provided that can include nanoscale particles including metal cations such as cerium having an average particle size of less than 10 nm. The nanoscale particles can include cerium and oxygen.

Methods for forming nanoparticles are provided. The methods can include exposing a metal cation within a solution to radiation to form metal nanoparticles that can include metal cations. The methods can include exposing a cerium salt solution to radiation to form the nanoparticles. The methods can include exposing solvated metal cations to radiation to precipitate nanoparticles that include metal cations such as Ce. The methods can include exposing the homogeneous solution to radiation to precipitate nanoparticles. The methods can include: providing an aqueous solution comprising metal cations; and increasing the pH of the aqueous solution with radiation to form nanoparticles that include metal cations.

Nanoparticle generators are provided. The generators can include: a reactant reservoir comprising a metal cation in solution; a fluid cell in fluid communication with the reactant reservoir; a radiation source operatively aligned with the fluid cell; and a product reservoir in fluid communication with the fluid cell.

8 Claims, 3 Drawing Sheets

(51) Int. Cl.
*A61K 9/16* (2006.01)
*C01F 17/00* (2006.01)
*B01J 19/08* (2006.01)

(52) U.S. Cl.
CPC ......... *B01J 19/081* (2013.01); *C01F 17/0043* (2013.01); *B01J 2219/0877* (2013.01); *B01J 2219/1203* (2013.01); *C01P 2004/64* (2013.01)

(58) Field of Classification Search
CPC ....... B01J 2219/1203; B01J 2219/0877; C01F 17/0043; C01P 2004/64
See application file for complete search history.

(56) References Cited

OTHER PUBLICATIONS

Tao, Yu, et al. "Preparation of shape-controlled CeO2 nanocrystals via microwave-assisted method." Materials Chemistry and Physics 124.1 (2010): 541-546.*
Pavelková, Tereza, et al. "E-beam and UV induced fabrication of CeO2, Eu2O3 and their mixed oxides with UO2." Radiation Physics and Chemistry 124 (2016): 252-257.*
Abellan et al. "Controlled Radiolytic Synthesis in the Fluid Stage, Towards Understanding the Effect of the Electron Beam in Liquids", Microscopy and Microanalysis vol. 21 (Suppl 3), Paper No. 1061, 2015, United Kingdom, pp. 2125-2126.
Abellan et al., "The Formation of Cerium(III) Hydroxide Nanoparticles by a Radiation Mediated Increase in Local pH", RSC Advances vol. 7, 2017, United Kingdom, pp. 3831-3837.
Albanese et al., "The Effect of Nanoparticle Size, Shape, and Surface Chemistry on Biological Systems", Annual Review of Biomedical Engineering vol. 14, 2012, United States, pp. 1-16.
Alili et al., "Combined Cytotoxic and Anti-invasive Properties of Redox-Active Nanoparticles in Tumor-Stroma Interactions", Biomaterials vol. 32, 2011, United Kingdom, pp. 2918-2929.
Baer, "Surface Characterization of Nanoparticles: Critical Needs and Significant Challenges", Journal of Surface Analysis vol. 17, No. 3, 2011, Japan, pp. 163-169.
Brivio et al., "Miniaturized Continuous Flow Reaction Vessels: Influence on Chemical Reactions", Lab on a Chip vol. 6, 2006, United Kingdom, pp. 329-344.
Brody et al., "Biotechnology at Low Reynolds Numbers", Biophysical Journal vol. 71, Dec. 1996, United States, pp. 3430-3441.
Chen et al., "Rare Earth Nanoparticles Prevent Retinal Degeneration Induced by Intracellular Peroxides", Nature Nanotechnology, 2006, United Kingdom, 9 pages.
Churski et al., "High-Throughput Automated Droplet Microfluidic System for Screening of Reaction Conditions", Lab on a Chip vol. 10, 2010, United Kingdom, pp. 816-818.
D'Angelo et al., "Cerium Oxide Nanoparticles Trigger Neuronal Survival in a Human Alzheimer Disease Model by Modulating BDNF Pathway", Current Nanoscience vol. 5, 2009, United Arab Emirates, pp. 167-176.
Deshpande et al., "Size Dependency Variation in Lattice Parameter and Valency States in Nanocrystalline Cerium Oxide", Applied Physics Letters vol. 87, 2005, United States, 3 pages.
Dutta et al., "Concentration of Ce3+ and Oxygen Vacancies in Cerium Oxide Nanoparticles", Chemistry of Materials vol. 18, 2006, United States, pp. 5144-5146.
Egorov et al., "Sequential Injection Renewable Separation Column Instrument for Automated Sorbent Extraction Separations of Radionuclides", Analytical Chemistry vol. 71, 1999, United States, pp. 345-352.
Esch et al., "Electron Localization Determines Defect Formation on Ceria Substrates", Science vol. 309, Jul. 2005, United States, pp. 752-755.
Estevez et al., "Neuroprotective Mechanisms of Cerium Oxide Nanoparticles in a Mouse Hippocampal Brain Slice Model of Ischemia", Free Radical Biology and Medicine vol. 51, 2011, Netherlands, pp. 1155-1163.
Hirst et al., "Anti-Inflammatory Properties of Cerium Oxide Nanoparticles", Small vol. 5, 2009, Germany, pp. 2848-2856.
Huebner et al., "Microdroplets: A Sea of Applications?", Lab on a Chip vol. 8, 2008, United Kingdom, pp. 1244-1254.
Jandik et al., "Initial Study of Using a Laminar Fluid Diffusion Interface for Sample Preparation in High-Performance Liquid Chromatography", Journal of Chromatography A vol. 954, 2002, Netherlands, pp. 33-40.
Jensen, "Microreaction Engineering—Is Small Better?", Chemical Engineering Science vol. 56, 2001, United Kingdom, pp. 293-303.
Ji et al., "Designed Synthesis of CeO2 Nanorods and Nanowires for Studying Toxicological Effects of High Aspect Ration Nanomaterials", ACS Nano vol. 6, No. 6, 2012, United States, pp. 5366-5380.
Karakoti et al., "Direct Synthesis of Nanoceria in Aqueous Polyhydroxyl Solutions", Journal of Physical Chemistry C vol. 111, 2007, United States, pp. 17232-17240.
Karakoti et al., "Preparation and Characterization Challenges to Understanding Environmental and Biological Impacts of Ceria Nanoparticles", Surface and Interface Analysis vol. 44, 2012, United States, pp. 882-889.
Karakoti et al., "Redox-Active Radical Scavenging Nanomaterials", Chemical Society Reviews vol. 39, 2010, United States, pp. 4422-4432.
Karakoti et al., "The Potential Toxicity of Nanomaterials—The Role of Surfaces", JOM vol. 58, Jul. 2006, United States, pp. 77-82.
Korsvik et al., "Superoxide Dismutase Mimetic Properties Exhibited by Vacancy Engineered Ceria Nanoparticles", Chemical Communications, 2007, United Kingdom, pp. 1056-1058.
Kuchibhatia et al., "Hierarchical Assembly of Inorganic Nanostructure Building Blocks to Octahedral Superstructures—A True Template-Free Self-Assembly", Nanotechnology vol. 18, 2007, United Kingdom, 4 pages.
Lam et al., "Culturing Aerobic and Anaerobic Bacteria and Mammalian Cells with a Microfluidic Differential Oxygenator", Analytical Chemistry vol. 81, 2009, United States, pp. 5918-5924.
Marre et al., "Synthesis of Micro and Nanostructures in Microfluidic Systems", Chemical Society Reviews vol. 39, 2010, United States, pp. 1183-1202.
Niu et al., "Cardioprotective Effects of Cerium Oxide Nanoparticles in a Transgenic Murine Model of Cardiomyopathy", Cardiovascular Research vol. 73, 2007, Netherlands, pp. 549-559.
Ozanich et al., "Rapid Multiplexed Flow Cytometric Assay for Botulinum Neurotoxin Detection using an Automated Fluidic Microbead-Trapping Flow Cell for Enhanced Sensitivity", Analytical Chemistry vol. 81, 2009, United States, pp. 5783-5793.
Sarathy et al., "Aging of Iron Nanoparticles in Aqueous Solution: Effects on Structure and Reactivity", Journal of Physical Chemistry C 112, 2008, United States, pp. 2286-2293.
Singh et al., "A Phosphate-Dependent Shift in Redox State of Cerium Oxide Nanoparticles and its Effects on Catalytic Properties", Biomateriais vol. 32, 2011, United Kingdom, pp. 6745-6753.
Song et al., "Millisecond Kinetics on a Microfluidic Chip Using Nanoliters of Reagents", Journal of the American Chemical Society vol. 125, 2003, United States, pp. 14613-14619.
Song et al., "Reactions in Droplets in Microfluidic Channels", Angewandte Chemie International Edition vol. 45, 2006, United Kingdom, pp. 7336-7356.
Suh et al., "A Valence Control Method Based on a Pt-Aided Hydrogen Peroxide Treatment for Yielding Tetravalent Neptunium and Plutonium in Nitric Acid Solutions", Bulletin of the Korean Chemical Society vol. 29, 2008, United States, pp. 475-478.
Sun et al., "Controlled Dispensing and Mixing of Pico- to Nanoliter Volumes using On-Demand Droplet-Based Microfluidics", Microfluidics and Nanofluidics vol. 15, 2013; Germany, pp. 117-126.
Sun et al., "Robust Extraction Interface for Coupling Droplet-Based and Continuous Flow Microfluidics", InTech, Advances in Microfluidics, 2012, Rijeka, Croatia, pp. 155-170.
Teh et al., "Droplet Microfluidics", Lab on a Chip vol. 8, 2008, United Kingdom, pp. 198-220.

(56) References Cited

OTHER PUBLICATIONS

Thomas et al., "Regulating Oxygen Levels in a Microfluidic Device", Analytical Chemistry vol. 83, 2011, United States, pp. 8821-8824.
Torigoe et al., "Microflow Reactor Synthesis of Palladium Nanoparticles Stabilized with Poly(Benzyl Ether) Dendron Ligands", Journal of Nanoparticle Research vol. 12, 2010, Netherlands, pp. 951-960.
Van Stroe-Biezen et al., "Diffusion Coefficients of Oxygen, Hydrogen Peroxide and Glucose in a Hydrogel", Analytica Chimica Acta vol. 273, 1993, Netherlands, pp. 553-560.
Varnum et al., "Enzyme-Amplified Protein Microarray and a Fluidic Renewable Surface Fluorescence Immunoassay for Botulinum Neurotoxin Detection using High-Affinity Recombinant Antibodies", Analytica Chimica Acta vol. 570, 2006, Netherlands, pp. 137-143.
Vincent et al., "Tuning Hydrated Nanoceria Surfaces: Experimental/Theoretical Investigations of Ion Exchange and Implications in Organic and Inorganic Interactions", Langmuir vol. 26, 2010, United States, pp. 7188-7198.
Warner et al., "A Flow-Through Ultrasonic Lysis Module for the Disruption of Bacterial Spores", Journal of the Association for Laboratory Automation vol. 14, Oct. 2009, United States, pp. 277-284.
Weigl et al., "Lab-on-a-Chip Sample Preparation using Laminar Fluid Diffusion Interfaces—Computational Fluid Dynamics Model Results and Fluidic Verification Experiments", Fresenius' Journal of Analytical Chemistry vol. 371, 2001, Germany, pp. 97-105.
Weigl et al., "Microfluidic Diffusion-Based Separation and Detection", Science vol. 283, 1999, United States, pp. 346-347.
Zhou et al., "Nanoceria Inhibit the Development and Promote the Regression of Pathologic Retinal Neovascularization in the Vldlr Knockout Mouse", PLoS ONE vol. 6, 2011, United States, 10 pages.
Abou-Hassan et al., "Microfluidics in Inorganic Chemistry", Angewandte Chemie International Edition vol. 49, 2010, United Kingdom, pp. 6268-6286.
Baer et al., "Application of Surface Chemical Analysis Tools for Characterization of Nanoparticles", Analytical and Bioanalytical Chemistry 396, 2010, Germany, pp. 983-1002.
Baret, "Surfactants in Droplet-Based Microfluidics", Lab on a Chip vol. 12, 2012, United Kingdom, pp. 422-433.
Bruckner-Lea et al., "Rotating Rod Renewable Microcolumns for Automated, Solid-Phase DNA Hybridization Studies", Analytical Chemistry vol. 72, 2000, United States, pp. 4135-4141.
Chandler et al., "Automated Immunomagnetic Separation and Microarray Detection of *E-Coli* O157:H7 from Poultry Carcass Rinse", International Journal of Food Microbiology vol. 70, 2001, Netherlands, pp. 143-154.
Chandler et al., "Renewable Microcolumns for Solid-Phase Nucleic Acid Separations and Analysis from Environmental Samples", TrAC Trends in Analytical Chemistry vol. 19, 2000, Netherlands, pp. 314-321.
Colon et al., "Protection from Radiation-Induced Pneumonitis using Cerium Oxide Nanoparticles", Nanomedicine-Nanotechnology Biology and Medicine vol. 5, 2009, Netherlands, pp. 225-231.
Das et al., "Auto-Catalytic Ceria Nanoparticles Offer Neuroprotection to Adult Rat Spinal Cord Neurons", Biomaterials vol. 28, 2007, United Kingdom, pp. 1918-1925.
Egorov et al., "Automated Radioanalytical System Incorporating Microwave-Assisted Sample Preparation, Chemical Separation, and On-Line Radiometric Detection for the Determination of Total 99Tc in Nuclear Waste Processing Streams", Analytical Chemistry vol. 84, 2012, United States, pp. 3090-3098.
Frenz et al., "Droplet-Based Microreactors for the Synthesis of Magnetic Iron Oxide Nanoparticles", Angewandte Chemie International Edition vol. 47, 2008, United Kingdom, pp. 6817-6820.
Grate et al., "Automated Radiochemical Separation, Analysis, and Sensing", Handbook of Radioactivity Analysis (3rd Ed.), Academic Press, 2012, San Diego, pp. 1179-1207.
Grate et al., "Automated Sample Preparation Method for Suspension Arrays using Renewable Surface Separations with Multiplexed Flow Cytometry Fluorescence Detection", Analytica Chimica Acta vol. 478, 2003, United States, pp. 85-98.
Grate et al., "Automating Analytical Separations in Radiochemistry", Analytical Chemistry vol. 70, 1998, United States, pp. 779A-788A.
Grate et al., "Automation of Extraction Chromatographic and Ion Exchange Separations for Radiochemical Analysis and Monitoring", Ion Exchange and Solvent Extraction, 2010, CRC Press: Boca Raton, Florida, pp. 515-562.
Grate et al., "Radionuclide Sensors for Environmental Monitoring: From Flow Injection Solid Phase Absorptiometry to Equilibration-Based Preconcentrating Minicolumn Sensors with Radiometric Detection", Chemical Reviews vol. 108, 2008, United States, pp. 543-562.
Grate et al., "Renewable Surface Fluorescence Sandwich Immunoassay Biosensor for Rapid Sensitive Botulinum Toxin Detection in an Automated Fluidic Format", Analyst vol. 134, 2009, United Kingdom, pp. 987-996.
Heckert et al., "The Role of Cerium Redox State in the SOD Mimetic Activity of Nanoceria", Biomaterials vol. 29, 2008, United Kingdom, pp. 2705-2709.
Hirst et al., "Bio-Distribution and In Vivo Antioxidant Effects of Cerium Oxide Nanoparticles in Mice", Environmental Toxicology vol. 28, 2011, United States, pp. 107-118.
Karakoti et al., "Nanoceria as Antioxidant: Synthesis and Biomedical Applications", JOM vol. 60, 2008, United States, pp. 33-37.
Karakoti et al., "PEGylated Inorganic Nanoparticles", Angewandte Chemie—International Edition vol. 50, 2011, United Kingdom, pp. 1980-1994.
Karakoti et al., "PEGylated Nanoceria as Radical Scavenger with Tunable Redox Chemistry", Journal of the American Chemical Society vol. 131, Oct. 2009, United States, pp. 14144-14145.
Karakoti et al., "Rare Earth Oxides as Nanoadditives in 3-D Nanocomposite Scaffolds for Bone Regeneration", Journal of Materials Chemistry vol. 20, 2010, United Kingdom, pp. 8912-8919.
Karakoti et al., "Self-Assembly of Cerium Oxide Nanostructures in Ice Molds", Small vol. 4, 2008, Germany, pp. 1210-1216.
Kelly et al., "Capillary-Based Multi Nanoelectrospray Emitters: Improvements in Ion Transmission Efficiency and Implementation with Capillary Reversed-Phase LC-ESI-MS", Analytical Chemistry vol. 80, 2008, United States, pp. 143-149.
Kelly et al., "Dilution-Free Analysis from Picoliter Droplets by Nano-Electrospray Ionization Mass Spectrometry", Angewandte Chemie vol. 121, 2009, United Kingdom, pp. 6964-6967.
Kelly et al., "Elastomeric Microchip Electrospray Emitter for Stable Cone-Jet Mode Operation in the Nanoflow Regime", Analytical Chemistry vol. 80, 2008, United States, pp. 3824-3831.
Kelly et al., "Nanoelectrospray Emitter Arrays Providing Interemitter Electric Field Uniformity", Analytical Chemistry vol. 80, 2008, United States, pp. 5660-5665.
Kong et al., "Nanoceria Extend Photoreceptor Cell Lifespan in Tubby Mice by Modulation of Apoptosis/Survival Signaling Pathways", Neurobiology of Disease vol. 42, 2011, United States, pp. 514-523.
Kosmulski, "pH-Dependent Surface Charging and Points of Zero Charge: III. Update", Journal of Colloid and Interface Science vol. 298, 2006, United States, pp. 730-741.
Kuchibhatla et al., "Influence of Aging and Environment on Nanoparticle Chemistry: Implication to Confinement Effects in Nanoceria", The Journal of Physical Chemistry C vol. 116, 2012, United States, pp. 14108-14114.
Kuchibhatla et al., "Symmetry-Driven Spontaneous Self-Assembly of Nanoscale Ceria Building Blocks to Fractal Superoctahedra", Crystal Growth & Design vol. 9, 2009, United States, pp. 1614-1620.
Marginean et al., "Analytical Characterization of the Electrospray Ion Source in the Nanoflow Regime", Analytical Chemistry vol. 80, 2008, United States, pp. 6573-6579.
O'Hara et al., "Automated Radioanalytical System for the Determination of 90Sr in Environmental Water Samples by 90Y Cherenkov Radiation Counting", Analytical Chemistry vol. 81, 2009, United States, pp. 1228-1237.
O'Hara et al., "Quantification of Technetium-99 in Complex Groundwater Matrixes using a Radiometric Preconcentrating Minicolumn

(56) References Cited

OTHER PUBLICATIONS

Sensor in an Equilibration-Based Sensing Approach", Analytical Chemistry vol. 81, 2009, United States, pp. 1068-1078.

Pirmohamed et al., "Nanoceria Exhibit Redox State-Dependent Catalase Mimetic Activity", Chemical Communications vol. 46, 2010, United Kingdom, pp. 2736-2738.

Singh et al., "Unveiling the Mechanism of Uptake and Sub-Cellular Distribution of Cerium Oxide Nanoparticles", Molecular Biosystems vol. 6, 2010, United Kingdom, pp. 1813-1820.

Sun et al., "Hydrodynamic Injection with Pneumatic Valving for Microchip Electrophoresis with Total Analyte Utilization", Electrophoresis vol. 32, 2011, United Kingdom, pp. 1610-1618.

Sun et al., "Membrane-Based Emitter for Coupling Microfluidics with Ultrasensitive Nanoelectrospray Ionization-Mass Spectrometry", Analytical Chemistry vol. 83, 2011, United States, pp. 5797-5803.

Sun et al., "Ultrasensitive Nanoelectrospray Ionization-Mass Spectrometry using Poly(Dimethylsiloxane) Microchips with Monolithically Integrated Emitters", Analyst vol. 135, 2010, United Kingdom, pp. 2296-2302.

Tarnuzzer et al., "Vacancy Engineered Ceria Nanostructures for Protection from Radiation-Induced Cellular Damage", Nano Letters vol. 5, 2005, United States, pp. 2573-2577.

Tsunoyama et al., "Microfluidic Synthesis and Catalytic Application of PVP-Stabilized, ~1 nm Gold Clusters", Langmuir vol. 24, 2008, United States, pp. 11327-11330.

Wagner et al., "Continuous Synthesis of Gold Nanoparticles in a Microreactor", Nano Letters vol. 5, 2005, United States, pp. 685-691.

Wheeler et al., "Microfluidic Labeling of Biomolecules with Radiometals for use in Nuclear Medicine", Lab on a Chip vol. 10, 2010, United Kingdom, pp. 3387-3396.

Wu et al., "Oxidation State and Lattice Expansion of $CeO_{2-x}$ Nanoparticles as a Function of Particle Size", Physical Review B vol. 69, 2004, United States, 9 pages.

* cited by examiner

NANOPARTICLES, METHODS FOR PRODUCING NANOPARTICLES AND NANOPARTICLE GENERATORS

CROSS REFERENCE TO RELATED APPLICATION

This application claims priority to U.S. provisional patent application Ser. No. 62/327,614 which was filed Apr. 26, 2016, entitled "Cerium Nanoparticles, Methods for Producing Cerium Nanoparticles and Cerium Nanoparticle Generators", the entirety of which is incorporated by reference herein.

STATEMENT AS TO RIGHTS TO INVENTIONS MADE UNDER FEDERALLY-SPONSORED RESEARCH AND DEVELOPMENT

This invention was made with Government support under Contract DE-AC0576RL01830 awarded by the U.S. Department of Energy. The Government has certain rights in the invention.

TECHNICAL FIELD

The present disclosure provides nanoparticle synthesis methods, compositions and methods, and in particular embodiments synthesis methods, compositions, and generators for nanoscale particles that can include metal cations such as cerium, and/or in particular embodiments nanoscale particles that can include cerium and oxygen.

BACKGROUND

Biomedical nanoparticles promise a revolution in therapeutics and imaging. Nanoscale particles that include cerium and oxygen can be referred to as cerium oxide nanoparticles (CNPs), or "nanoceria" represent a case in point. These materials can be scavengers for reactive oxygen species (ROS), which is their desired antioxidant activity for biomedical applications in cancer therapy, neuroprotection, and other conditions. However, depending on the synthesis, they may instead be toxic materials leading to oxidative stress, or they can be biomedically inert. Their activities vary from batch to batch, change over time, and there are no known methods to stop the time-dependent aging processes that alter the desired biomedical properties. The fact that nanoparticle properties vary with synthesis conditions, and then vary in properties with time after synthesis, represents a major obstacle to the translation of nanoparticle therapeutics into practice. Indeed, even biomedical research with such nanoparticles is hampered due to poor reproducibility of nanoparticle materials. Solutions are needed to overcome the problems associated with general biomedical nanoparticle synthesis.

Biomedical nanoparticles described generically as cerium oxide nanoparticles, or nanoceria, are not strictly $CeO_2$. Rather they are nanoscale particles that include cerium and oxygen, where the cerium may exist as Ce III or Ce IV or as a mixture of Ce III and Ce IV. The oxygen may be present as oxyanions or hydroxide anions, for example. In some compositions, oxygen can be present as peroxy species. For biomedical efficacy, it is believed that Ce III must be present as part of the nanoparticle to obtain antioxidant activity, and that small irregular nanoparticles are ideal. Biomedical nanoparticles often have more cerium III than cerium IV.

SUMMARY OF THE DISCLOSURE

Compositions are provided that can include nanoscale particles including metal cations such as cerium having an average particle size of less than 10 nm. The nanoscale particles can include cerium and oxygen.

Methods for forming nanoparticles are provided. The methods can include exposing a metal cation within a solution to radiation to form metal nanoparticles that can include metal cations.

Methods for forming nanoparticles are provided with the nanoparticles including cerium. The methods can include exposing a cerium salt solution to radiation to form the nanoparticles.

Methods for forming nanoparticles that include metal cations are provided. The methods can include exposing solvated metal cations to radiation to precipitate nanoparticles that include metal cations such as Ce.

Methods for precipitating nanoparticles from a homogeneous solution are provided. The methods can include exposing the homogeneous solution to radiation to precipitate nanoparticles.

Methods for forming nanoparticles that include metal cations are provided. The methods can include: providing an aqueous solution comprising metal cations; and increasing the pH of the aqueous solution with radiation to form nanoparticles that include metal cations.

Nanoparticle generators are provided. The generators can include: a reactant reservoir comprising a metal cation in solution; a fluid cell in fluid communication with the reactant reservoir; a radiation source operatively aligned with the fluid cell; and a product reservoir in fluid communication with the fluid cell.

DRAWINGS

Embodiments of the disclosure are described below with reference to the following accompanying drawings.

Figure 4:
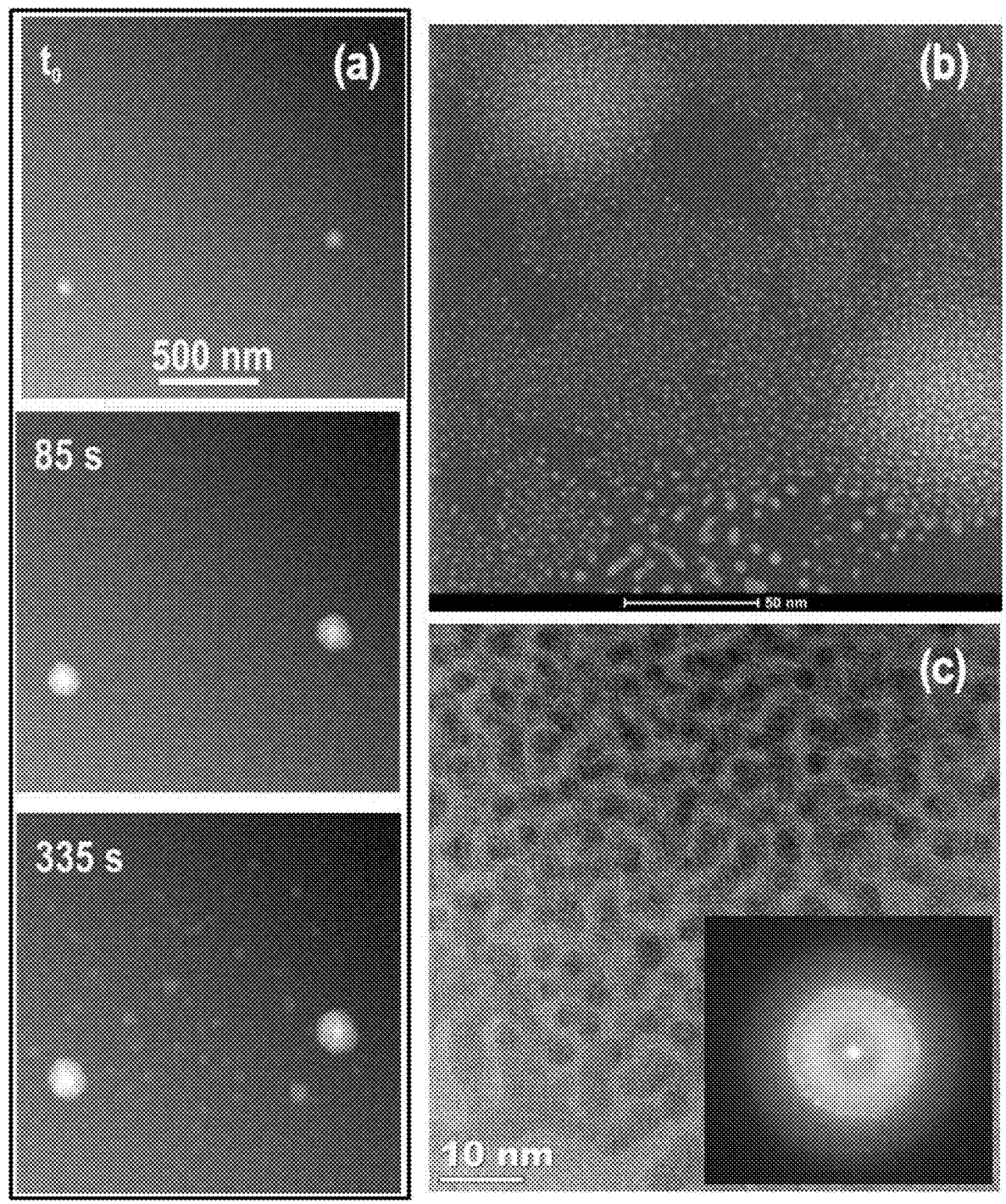

FIG. 4. includes snapshots to, 85 sec., and 335 sec.; reaction products, and high resolution imagery of $Ce(OH)_3$.

DESCRIPTION

This disclosure is submitted in furtherance of the constitutional purposes of the U.S. Patent Laws "to promote the progress of science and useful arts" (Article 1, Section 8).

Figure 1:
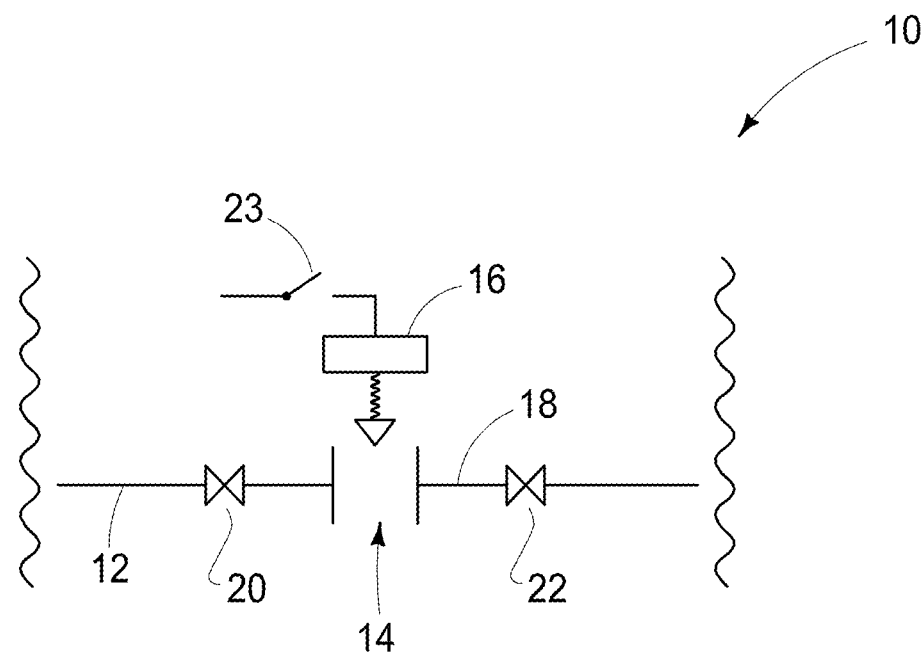
FIG. 1 is an example nanoparticle generator according to an embodiment of the disclosure.

The compositions, methods, and generators will be described with reference to FIGS. 1-4. Referring first to FIG. 1, a generator 10 is depicted for example purposes and use in describing nanoparticles generators and methods of forming nanoparticles according to embodiments of the disclosure. Generator 10 can include a reactant reservoir 12 that can contain and/or transport a metal cation in solution. In fluid communication with reservoir 12 can be fluid cell 14, which can also be in fluid communication with product reservoir 18. Fluid cell 14 can also be considered a fluid stage. Operatively aligned with fluid cell 14 can be a radiation source 16. Generator 10 and methods can be operated in batch or flow as desired. To facilitate batch or flow operations valves 20 and 22 can be manipulated to provide reactants to fluid cell 14 and/or products from product reservoir 18. Additionally, radiation source 16 can be operated with an on/off switch 23 as nanoparticle generation is desired. In accordance with example implementations, radiation source 16 includes operator controls configured to allow on-demand radiation to fluid cell 14. Solution from the reactant reservoir can be irradiated from the radiation source with e-beams, x-rays, nuclear radiation, gamma rays, and/or alpha particles to provide radiolysis. This irradiation can be manipulated to provide the nanoparticles on demand. As an example, the precursor solutions can be irradiated using 300 kV electron beam provided from a scanning transmission electron microscope (STEM).

In at least one example implementation, product reservoir 18 can be operatively coupled to a nanoparticle administration assembly (not shown) via valve 22.

Figure 2:
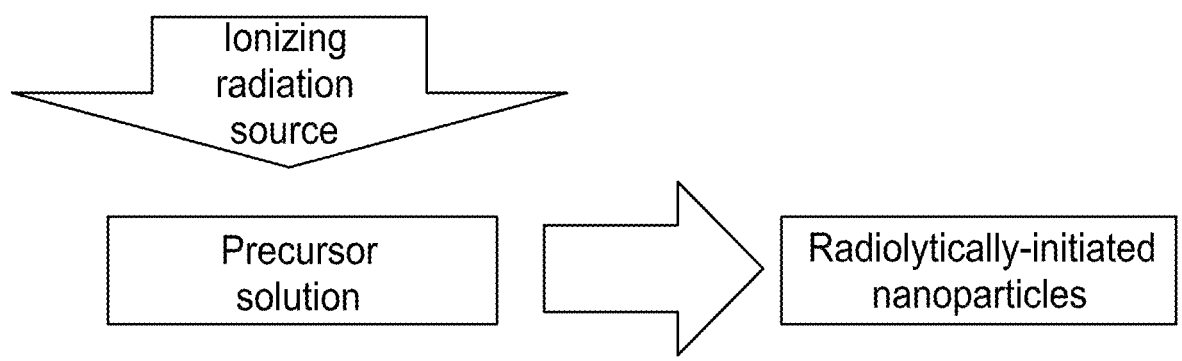
FIG. 2 is an example nanoparticle generator and/or method according to an embodiment of the disclosure.

With reference to FIG. 2, an example generator and/or method for producing cerium nanoparticles are provided. As a generator of nanoparticles, the generator can provide a precursor solution that can be irradiated to form the nanoparticles of the present disclosure.

Methods for forming the nanoparticle compositions of the present disclosure can include methods of forming nanoparticles, methods of forming nanoparticles that include metal cations such as cerium, methods of forming nanoparticles that can include cerium and oxygen, and/or methods of precipitating nanoparticles from homogeneous solutions.

One or more of the methods can include providing an aqueous reactant solution. The aqueous reactant solution can include a cation such as a metal cation. The cation may be associated with an anion and together the cation and anion can form a salt of the metal cation. The solution can be homogeneous in that the solution is entirely liquid without precipitates. In accordance with example implementations, the cations can be solvated within the solution. The solution can have an acidic pH, or a pH below 7, for example, but may also have a neutral or basic pH, or a pH above 7.

The reactant solution can include a Ce cation such as Ce III cation. The cation of the solution can be associated with a nitrate anion(s). The reactant solution can be, for example, Ce(III)nitrate in deionized water ($Ce(NO_3)_3 \cdot 6H_2O$). The salt can be provided at a concentration of 0.1 mM. The pH of the reactant solution can be 5.2.

In accordance with example implementations, the reactant solution can be exposed to radiation. Radiolysis of the reactant solutions can be initiated with ionizing radiation for example. The primary species produced by the radiation of $H_2O$ are: $e^-$(aqueous), $H_3O^+$, $H^-$, $OH^-$, $H_2$, $H_2O_2$ and $HO_2$. Conventionally, radiolysis of water leads to pH changes to lower values, i.e., becoming more acidic. In accordance with the present disclosure, exposing the reactant solution to radiation can raise the pH of the solution to a higher pH, for example, from acidic (below 7) to less acidic, from acidic to basic (above 7) and/or from basic to more basic. Example exposures can change the pH from about 5.2 to about 7.2. The pH may also be changed to as high as 10 or higher, for example.

Exposure of the homogenous reactant solution to radiation can precipitate nanoparticles from the homogenous solution thereby generating a heterogeneous solution having particles. Conventional metal cations in solution, exposed to radiolytic conditions, lead to particles having metals with a zero valency. In accordance with the present disclosure, the particles formed can be nanoparticles have a metal ion, or a charged state such as a metal cation. The nanoparticles formed can include metal cations of the same valence as the metal cations of the reactant solutions, for example. Accordingly, a III cation in solution can be used to generated a III cation of the nanoparticle. More specifically, Ce III cations of the reactant solution can be part of nanoparticles that can include Ce III cations. Some or all of the Ce of the nanoparticles can have a III valence state while some of the particles may have a IV valence state. The nanoparticles can include the ion and oxygen, such as cerium and oxygen.

In accordance with example implementations of the method, at low beam dose (dose rate of ~4 $e^-/Å^2$ per frame and beam current of 6 pA) no particle growth was observed in situ even upon extended irradiation. At sufficient dose, in situ nanoparticle formation in the beam area is observed. Starting with cerium (III) nitrate at 0.1 mM concentration, the electron beam current was increased from 6 pA to 80.5 pA, while keeping the electron dose rate at ~4 $e^-/Å^2$ per frame. Particles were observed by in situ TEM to form in solution with sizes being in the 1-4 nm range and a mean diameter of 2.9 nm.

Figure 3:
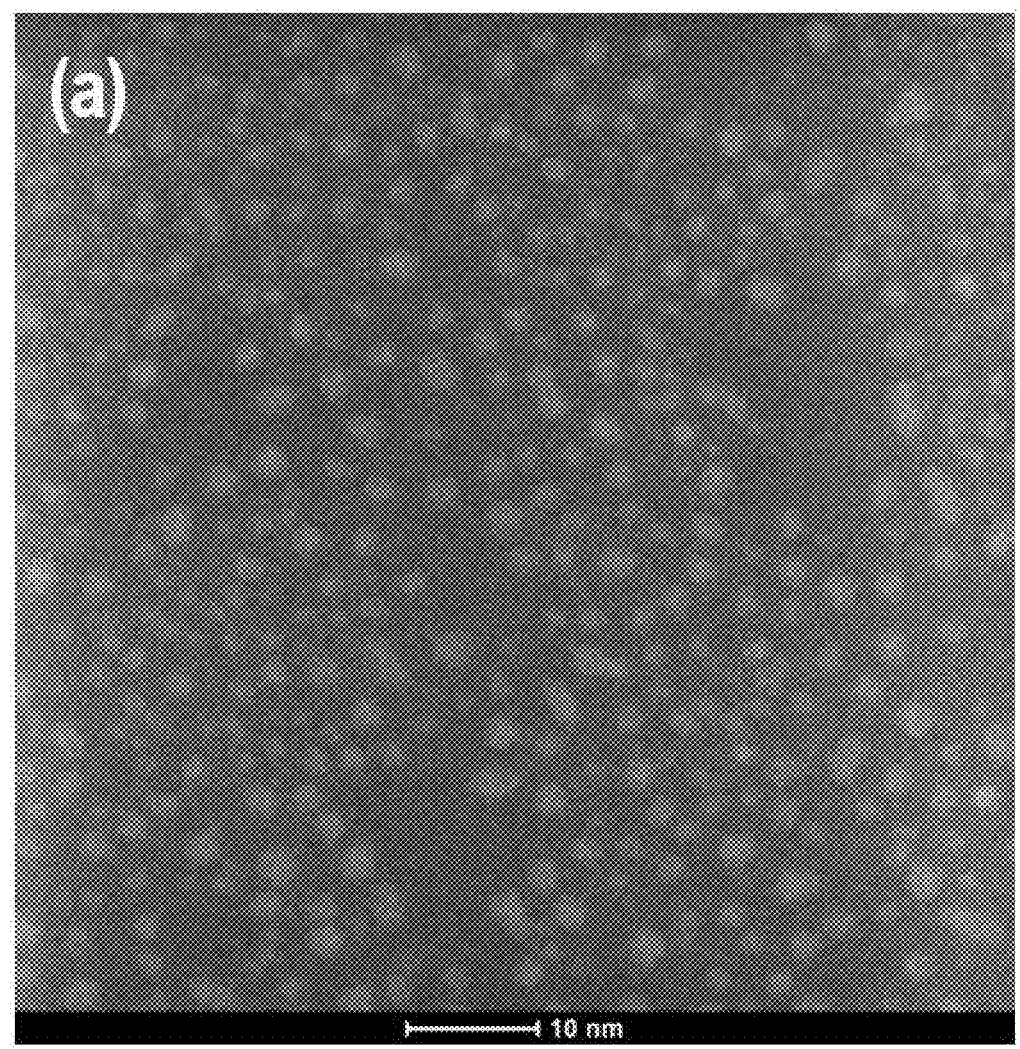
FIG. 3 is STEM imagery of reaction products, particle distribution, and monocrystalline $Ce(OH)_3$.
Figure 3:
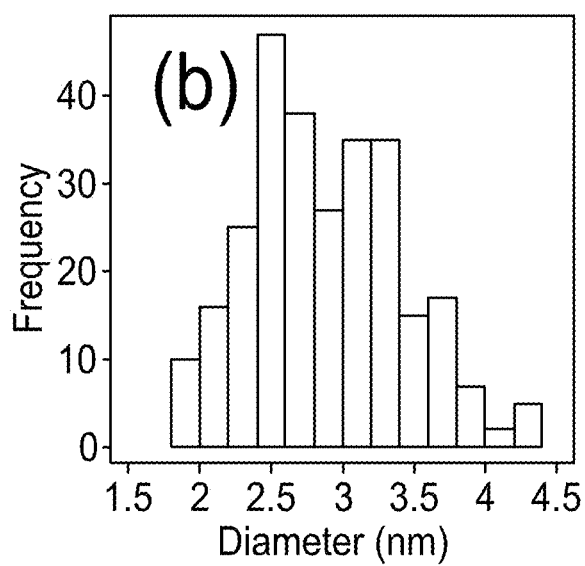
Figure 3:
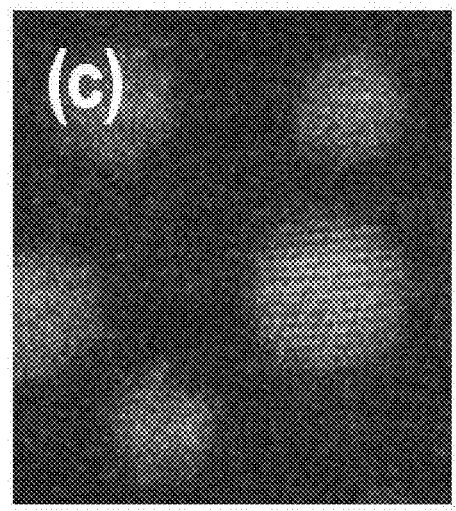

Results for particle growth in the electron beam are shown in FIGS. 3 and 4. Growth of individual nanoparticles is shown in FIG. 3: (a) Dark Field STEM image showing the reaction products of a growth experiment using the Ce(III) precursor solution. An electron beam current of 80.5 pA; Magnification 40,000×; Pixel dwell time: 3 µs were used to give an electron dose rate of 4.4 $e^-/Å^2$ per frame. (b) Particles size distribution included a total of 279 particles in the analysis. The minimum diameter measured was 1.9 nm; median: 2.8 nm; mean value: 2.9 nm; max value: 4.342 nm; standard deviation: 0.5 nm. (c) Particles are monocrystalline Ce(OH)3.

Extended irradiation leads to particle coalescence and reorientation as shown in FIG. 4; hence, the dose rate and time influence the final nanoparticle characteristics. FIG. 4 (*a*) Snapshots of a dark field (DF) STEM in situ movie of the particles in solution showing that extended irradiation times produce particle mediated growth. FIG. 4 (*b*) Reaction products of the growth experiments showing that brighter areas are particles that undergo coalescence, resulting on an increased particle size, especially in more populated areas. They also reorient themselves along with the electron beam. FIG. 4 (*c*) High resolution TEM (HRTEM) image showing a detail of the areas where agglomeration has occurred. FFT showing the $Ce(OH)_3$ structure.

After dismantling and drying the sample, images were taken and fast Fourier transform (FFT) was used to determine diffraction features from the sample images. The solids formed in the irradiated area were determined to be of hexagonal structure, corresponding to $Ce(OH)_3$. The brightest spots of the FFT are the (102) family of planes of the hexagonal $Ce(OH)_3$ structure. (Note: $Ce_2O_3$ and $Ce(OH)_3$ are isostructural and have very similar lattice constant, but $Ce_2O_3$ is very unstable and unlikely to be formed.) Only the irradiated area on the $SN_x$ membrane surface was covered with $Ce(OH)_3$ particles. Non irradiated areas examined after dismantling and drying were found to have $CeO_2/Ce(OH)_4$ precipitates present. Control experiments show that these $CeO_2/Ce(OH)_4$ precipitates arise as artifacts of dismantling and drying, rather than as radiolytic products.

Therefore, the particles formed in situ, only in the irradiated area, are attributed to radiolytic processes and identified as $Ce(OH)_3$ nanoparticles, containing Ce and Oxygen atoms, where there are Ce atoms in the Ce(III) valence state.

In accordance with at least the methods provided herein compositions are provided. The compositions can include nanoparticles that can include cerium and oxygen and have an average particle size of less than 10 nm. The nanoparticles can include cerium in the III and/or IV valence states.

However, the cerium III composition of the nanoparticles can be greater than the cerium IV composition.

The nanoparticles can be nanoscale particles that can include metals such as metal cations. The metal can be Ce and the cation can be Ce III and/or Ce IV. The particles can further include oxygen, such particles can include cerium and oxygen. For example, the particles can include cerium III hydroxide. These nanoparticles can have an average particle size of less than 5 nm or an average particle size of 1-4 nm or even a mean particle size of 2.9 nm.

These nanoparticles can be nanoscale particles and can include cerium and oxygen. The Ce of the nanoparticle can be of the Ce(III) variety, such as $Ce(OH)_3$. The nanoparticle may also contain both Ce(III) and Ce(IV), with the Ce(III) being the predominant species. The nanoparticles can be nanoscale particles that include metal ions, and can be bio medically therapeutic nanoparticles.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect.

The invention claimed is:

1. A method for forming nanoparticles, the method comprising: exposing a cerium salt solution to an electron beam to form cerium nanoparticles having a particle size between 1 and 4 nm.

2. The method of claim 1 wherein the cerium salt comprises Ce Ill.

3. The method of claim 1 wherein the cerium salt is present in the solution in an amount of at least 0.1 mM.

4. The method of claim 1 wherein the cerium salt solution has a pH below 7.

5. The method of claim 1 wherein the cerium salt solution comprises nitrate.

6. The method of claim 1 wherein the cerium within the cerium salt solution has the same valence state as the cerium comprised by the nanoparticle.

7. The method of claim 1 further comprising raising the pH of the solution upon formation of the nanoparticle.

8. The method of claim 1 wherein the electron beam is 80.5 pA.

* * * * *